US009145527B2

(12) United States Patent
Lu

(10) Patent No.: US 9,145,527 B2
(45) Date of Patent: Sep. 29, 2015

(54) METHOD FOR PREPARING HIGH PURITY BIODIESEL

(75) Inventor: Xinuo Lu, Beijing (CN)

(73) Assignee: BEIJING QINGYANLIHUA PETROLEUM CHEMISTRY CO., LTD., Beijing (CN)

(*) Notice: Subject to any disclaimer, the term of this patent is extended or adjusted under 35 U.S.C. 154(b) by 0 days.

(21) Appl. No.: 14/237,888

(22) PCT Filed: Aug. 9, 2012

(86) PCT No.: PCT/CN2012/079875
§ 371 (c)(1),
(2), (4) Date: Feb. 10, 2014

(87) PCT Pub. No.: WO2013/020514
PCT Pub. Date: Feb. 14, 2013

(65) Prior Publication Data
US 2014/0194634 A1 Jul. 10, 2014

(30) Foreign Application Priority Data
Aug. 10, 2011 (CN) .......................... 2011 1 0228437

(51) Int. Cl.
| *C10L 1/02* | (2006.01) |
| *C07C 67/03* | (2006.01) |
| *C11C 1/10* | (2006.01) |
| *C11C 3/00* | (2006.01) |
| *C11C 3/10* | (2006.01) |
| *C11B 13/00* | (2006.01) |
| *C07C 67/02* | (2006.01) |
| *C07C 67/08* | (2006.01) |

(52) U.S. Cl.
CPC . *C10L 1/02* (2013.01); *C07C 67/03* (2013.01); *C10L 1/026* (2013.01); *C11B 13/00* (2013.01); *C11C 1/10* (2013.01); *C11C 3/003* (2013.01); *C11C 3/10* (2013.01); *C07C 67/02* (2013.01); *C07C 67/08* (2013.01); *Y02E 50/13* (2013.01); *Y02W 30/74* (2015.05)

(58) Field of Classification Search
None
See application file for complete search history.

(56) References Cited

U.S. PATENT DOCUMENTS 4,698,186 A * 10/1987 Jeromin et al. ............... 554/174
5,536,856 A * 7/1996 Harrison et al. ............. 554/164

(Continued)

FOREIGN PATENT DOCUMENTS

CN  101020838 A  8/2007
CN  102311883 A  1/2012

OTHER PUBLICATIONS

Shouquan, L., CN 101020838 A, Biodiesel oil preparing process and apparatus, 2007, English Translation, 7 pages.*

(Continued)

*Primary Examiner* — Yate K Cutliff
(74) *Attorney, Agent, or Firm* — Eagle IP Limited; Jacqueline C. Lui

(57) ABSTRACT

Disclosed is a method for preparing high purity biodiesel from crude oils. The method comprises the steps of: pre-treating the crude oil raw material to remove impurities; pre-esterifying the pre-treated crude oil raw material under the effect of a catalyst of concentrated sulfuric acid; and then carrying out an ester exchange reaction in the presence of an alkali catalyst; recycling methanol, and separating glycerol, so as to obtain a crude fatty acid methyl ester; and subjecting the obtained fatty acid methyl ester to purification, distillation and segmentation to obtain a high-purity fatty acid methyl ester.

9 Claims, 2 Drawing Sheets

(56) References Cited

U.S. PATENT DOCUMENTS

| | | | |
|---|---|---|---|
| 6,965,043 B1 * | 11/2005 | Kenneally et al. | 554/167 |
| 7,700,793 B2 * | 4/2010 | Iyer | 554/174 |
| 2010/0043280 A1 | 2/2010 | Morris | |
| 2010/0205853 A1 * | 8/2010 | Rao et al. | 44/388 |

OTHER PUBLICATIONS

Wang, Lijun. Energy Efficiency and Management in Food Processing Facilities, 2008, 420-422, Taylor & Francis Group, LLC, Boca Raton, FL.

* cited by examiner

METHOD FOR PREPARING HIGH PURITY BIODIESEL

CROSS-REFERENCE TO RELATED APPLICATION

The present application claims priority under 35 U.S.C. §119 to Chinese Patent Application No. 201110228437.7 filed on Aug. 10, 2011. The content of the application is incorporated herein by reference in its entirety.

TECHNICAL FIELD

The present invention relates to a method for preparing high purity biodiesel. The method obtains high-purity fatty acid methyl ester (i.e. biodiesel) by pre-esterification reaction and ester exchange reaction using cheap raw materials such as crude oils (for example trench oil, acid oil, etc.).

BACKGROUND ART

The energy is a lifeline of the development of a country. With the rapid development of social economy, the shortage of commonly-used fossil resources such as petroleum, natural gas, coal, etc. at present is growing. Meanwhile, the use of large amounts of fossil resources results in many hazards to environment, such as green house effect, acid rain, etc. Furthermore, related industries, such as catering industry, food industry, etc., produce lots of waste animal and plant oils every day. Such waste oils generally contain a large amount of impurities, and part thereof is recycled to manufacture soap, part thereof is directly discharged without recycling and treating, thereby causing an environmental pollution, and part thereof goes back to dinner tables. Therefore, it has been paid more and more attention by people to how to sufficiently and effectively utilize waste animal and plant oils, so as to reduce the pollution of waste animal and plant oils to the environment such as water area, etc. and the harm to human body, and guarantee food safety so as to realize resource recycling.

The biodiesel, i.e. fatty acid methyl ester, has chemical formula of $RCOOCH_3$ (wherein R is $C_{12-17}$), is prepared mainly from plant oils (rice bran oil, cotton seed oil, sea kale oil, peanut oil, rapeseed oil, soybean oil, sunflower seed oil, etc.) or animal fats, is a diesel substitute obtained from renewable biomass resource and having property similar to diesel, and is a kind of renewable biomass resource. The main ingredients of the biodiesel are ester substances, such as methyl ester or ethyl ester formed of long-chain fatty acid. The biodiesel utilizes alcohols substance (methanol or ethanol) to proceed ester exchange reaction (transesterification) with the main ingredient (triglyceride) in natural plant oils or animal fats, substitutes glyceryl on long-chain fatty acid with methoxyl, and breaks triglyceride into multiple long-chain fatty acid methyl esters, so as to shorten the length of carbon chain, reduce the viscosity of oil material, improve the flowability and vaporability of oil material and thereby achieve the requirement of using as fuel.

Compared with fossil diesel, the biodiesel has similar ignition performance, heat value and dynamic property, far less corrosivity to engine and higher safety, thus it can be directly used as fuel without making any modification to existing diesel engine and does not cause any harmful effect on the engine. Moreover, the biodiesel can be mixed with fossil diesel at any ratio, which can not only reduce the emission of substances in tail gas harmful to the environment, but also effectively lower the use cost and reduce the overdependence on the fossil energy.

The biodiesel is derived from renewable biomass resources, thus not containing the substances such as sulfur, aromatic hydrocarbon, etc. commonly found in the fossil diesel. The biodiesel has a short carbon chain, contains oxygen itself and can be completely combusted, so as not to produce atmospheric pollutants such as $SO_x$, aromatic hydrocarbon, polycyclic aromatic hydrocarbon, etc., averagely reduce waste gas by above 45%, and effectively reduce the hazard of tail gas to the environment. The use of biodiesel can effectively reduce the concentrations of CO and TPM in tail gas, and the contribution of the biodiesel to green house effect is only 25% or lower of that of fossil diesel. Moreover, the biodiesel also has excellent biodegradability compared with fossil diesel.

The biodiesel has good environmental protection performance. It has a low sulfur content. The amount of sulfur dioxide and sulfide emitted by the biodiesel upon combustion is reduced by about 30% compared to common diesel. The biodiesel has oxygen content up to 11%, and good ignition performance, so that the harmful substances such as HC, CO, etc. discharged during combustion are greatly reduced compared to common diesel. The substances discharged by the biodiesel upon combustion contain no harmful substances such as sulfur dioxide, lead, halogen, etc, which is very favorable to environmental protection. Hence, the biodiesel is renewable environmentally-friendly fuel, and has good application prospect.

At present, the methods for preparing biodiesel mainly include: 1) esterification method for performing esterification reaction using oils and fats and methanol in the presence of acid catalyst; 2) ester exchange method for performing ester exchange reaction using oils and fats and methanol in the presence of alkali catalyst; 3) as to waste oil having many impurities and especially high free fatty acid contents, such as trench oil, generally esterification is performed first, and then alkali catalyzed ester exchange is performed, instead of directly performing ester exchange reaction by adopting alkali catalyst.

Chinese patent application CN 101906355A discloses a method for preparing biodiesel by utilizing food waste recycling oil. The method comprises pre-treating dining waste recycled oil using 1.5 wt % of 98% concentrated sulfuric acid, then esterifying the pre-treated dining waste recycled oil using 5 wt % of concentrated sulfuric acid based on the weight of raw material under the temperature of 65° C. for 2 h, transferring into an acid-catalyzed settlement separator, performing ester exchange using 1 wt % of 95% solid sodium hydroxide based on the weight of raw material under the temperature of 65° C. for 30 min, separating crude biodiesel through an alkali-catalyzed settlement separator, washing the obtained crude biodiesel with 3% of 98% concentrated sulfuric acid based on the volume of the crude biodiesel in a water-washing neutralization tower, then washing with water, and heating to distill the upper-layer biodiesel to obtain the final product. The method performs esterification reaction and ester exchange reaction in different reaction kettles respectively, and separates intermediate products through two settlement separators, thus increasing equipment cost and energy consumption. The method requires water-washing neutralization after ester exchange. The total amount of added concentrated sulfuric acid reaches 9.5% of raw material, so as to produce a large amount of acid water during water washing process, thus a large amount of alkali is required for neutralization in latter sewage treatment, thereby increasing treatment cost. On the other hand, there exists some problems while independently using sodium hydroxide as catalyst in practical application: 1. long dissolving time and low dissolution rate of sodium hydroxide and methanol; 2. incomplete ester exchange reaction; 3. easy agglomeration of sodium salt, which results in serious pipeline blocking during ester exchange reaction when using soybean acid oil as raw material, thus not widely suitable for various raw materials; and 4. low separation speed of glycerol and fatty acid methyl ester produced in the reaction.

CN 101012388A discloses a method of manufacturing biological diesel oil from trench oil. The method comprises using trench oil and 0.2-3% solid acid catalyst (CaO or $SiO_2$) of porous carrier to perform esterification reaction under high temperature of above 95-130° C. for 1-4 h, then separating the solid acid catalyst, performing ester exchange reaction by using 3-5% solid alkaline catalyst (CaO or MgO) at 50-65° C. for 0.2-2 h, separating biological diesel oil in upper layer, separating the solid alkaline catalyst and glycerol from lower layer, and distilling to recover methanol. The method has a high esterification reaction temperature, and utilizes acid catalyst of porous carrier to increase reaction surface area, so as to accelerate esterification reaction speed. Although the method requires no neutralization and washing, it also requires two separation steps to separate the solid acid catalyst and the solid alkaline catalyst respectively. In addition, the method has no distillation, and no matter how thorough the ester exchange reaction is performed, it is impossible to convert all neutral oils and fats (triglyceride) into fatty acid methyl ester. In the patent, the biological diesel oil product is not subjected to distillation, and inevitably contains monoglyceride, diglyceride and triglyceride which are main ingredients of plant pitch, i.e., the patent does not separate plant pitch and biodiesel.

Therefore, there is a need for a method for preparing biodiesel with low equipment requirement, high conversion rates of esterification reaction and ester exchange reaction, low energy consumption and low cost.

SUMMARY OF THE INVENTION

The object of the present invention is to provide a method for preparing biodiesel from crude oils, comprising:

1) providing crude oil raw material, and pre-treating the crude oil raw material to remove impurities;

2) adding the pre-treated raw material into a reaction kettle;

3) pre-esterification step: adding methanol and 0.1-2 wt % concentrated sulfuric acid based on the pre-treated raw material into the reaction kettle, and maintaining at 70-100° C., preferably 70-80° C., for 30 min-2 h, wherein the weight ratio of methanol to the pre-treated raw material is (1:1)-(1:20);

4) esterification step of vapor phase: heating the above reaction system to 110-130° C., supplementing methanol in vapor phase from the bottom of the reaction kettle under atmospheric pressure, reacting under the temperature until the acid value of liquid phase system is ≤2, and stopping supplementing methanol;

5) ester exchange step: cooling the reaction material obtained in step 4) to below 70° C., adding mixture of potassium hydroxide and sodium hydroxide with equal weight ratio into the same reaction kettle to maintain pH of the reaction material in the reaction kettle at 8-9, and then reacting at 70-90° C., preferably 70-80° C., for 2-3 h;

6) recycling methanol, and separating glycerol via gravity settling, so as to obtain crude fatty acid methyl ester; and 7) subjecting the crude fatty acid methyl ester obtained in the step 6) to purification and distillation to obtain biodiesel.

The crude oil raw material is trench oil or acid oil.

The weight ratio of methanol to the pre-treated raw material in the step 3) is (1:15)-(1:4), more preferably (1:11)-(1:6).

The distillation of crude fatty acid methyl ester in the step 7) is performed at the temperature of 220-260° C. under the pressure of (−0.090)-(−0.099) MPa, so as to obtain biodiesel and plant pitch.

In the step 7), the crude fatty acid methyl ester is directly and continuously distilled and segmented into fraction products of four temperature intervals: a. ≤280° C.; b. 280-365° C.; c. 365-380° C.; and d. >380° C.

The recycling of methanol in the step 6) is accomplished via two steps: recycling at the temperature of 85-95° C. under atmospheric pressure and recycling at the temperature of 85-95° C. in vacuum.

The pre-treatment comprises one of water washing and dehydration in vacuum or the combination thereof.

The advantageous effects of the present invention are as following:

1. The preparation method of the present invention has wide raw material sources, and is suitable both for kitchen waste oil and for other waste animal and plant oils, acid oil, etc.

2. The method of the present invention has wide quality requirement for raw materials, which can be neutral oils and fats or waste oils and fats.

3. The method of the present invention has low energy consumption during production process, averagely consuming 250-300 kg of standard coal, 80-100 KWh of electricity and 100-150 kg of water while producing 1 t. of high-purity fatty acid methyl ester.

4. The method of the present invention has relatively simple production process, and relatively small equipment investment scale (less than 5 million per 10,000 t of the yield).

5. In the method of the present invention, pre-esterification reaction, esterification reaction of methanol vapor phase and ester exchange reaction can be accomplished in one step in the reaction kettle without transfering into another reaction kettle, thus reducing production intensity and sparing labor cost.

6. The present invention adopts mixed alkali of sodium hydroxide and potassium hydroxide (1:1) as catalyst, thereby greatly shortening the dissolving time of the catalyst and methanol, increasing the dissolution rate, making the ester exchange reaction more thorough, improving the blocking phenomenon of the pipeline, and making glycerol separation simpler.

7. The reaction process of the method of the present invention is carried out at medium-low temperature environment (70-130° C.), and thus has low energy consumption and guaranteed safety; and medium temperature and negative pressure adopted in the distillation process are beneficial to prevent the product from deteriorating due to sour regurgitation of reverse reaction.

8. The method of the present invention adopts lateral line continuous distillation fractionation, such that the products obtained by distillation of the crude fatty acid methyl ester are segmented into fraction products (lightweight grade, middleweight grade, and heavyweight grade fatty acid methyl ester of high purity, and plant pitch) of four temperature intervals: a. ≤280° C.; b. 280-365° C.; c. 365-380° C.; and d. ≥380° C., and the fatty acid methyl ester reach colorless and tasteless high-quality grade. The indexes of the products are superior to the requirements of GB/T 20828-2007.

9. The method of the present invention is simple and reliable, and has easily controlled reaction process, crude oil conversion rate up to over 97%, and finished product yield up to above 96%.

10. The main indexes of the biodiesel prepared according to the method of the present invention are superior to those of GB fossil diesel.

DETAILED DESCRIPTION OF THE INVENTION

Figure 1:
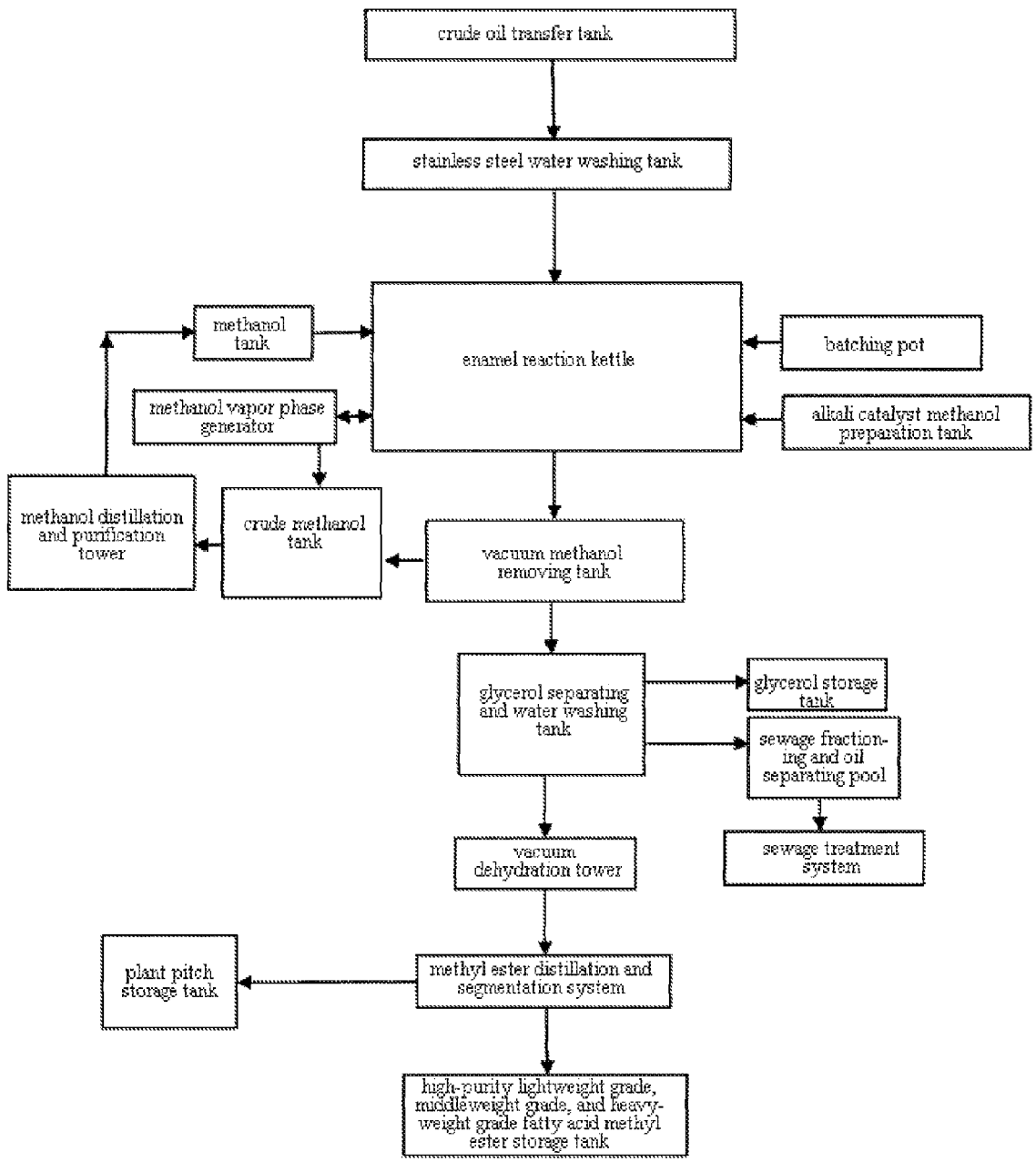
FIG. 1 is schematic diagram of equipment connection of an embodiment according to the method of the present invention.
Figure 2:
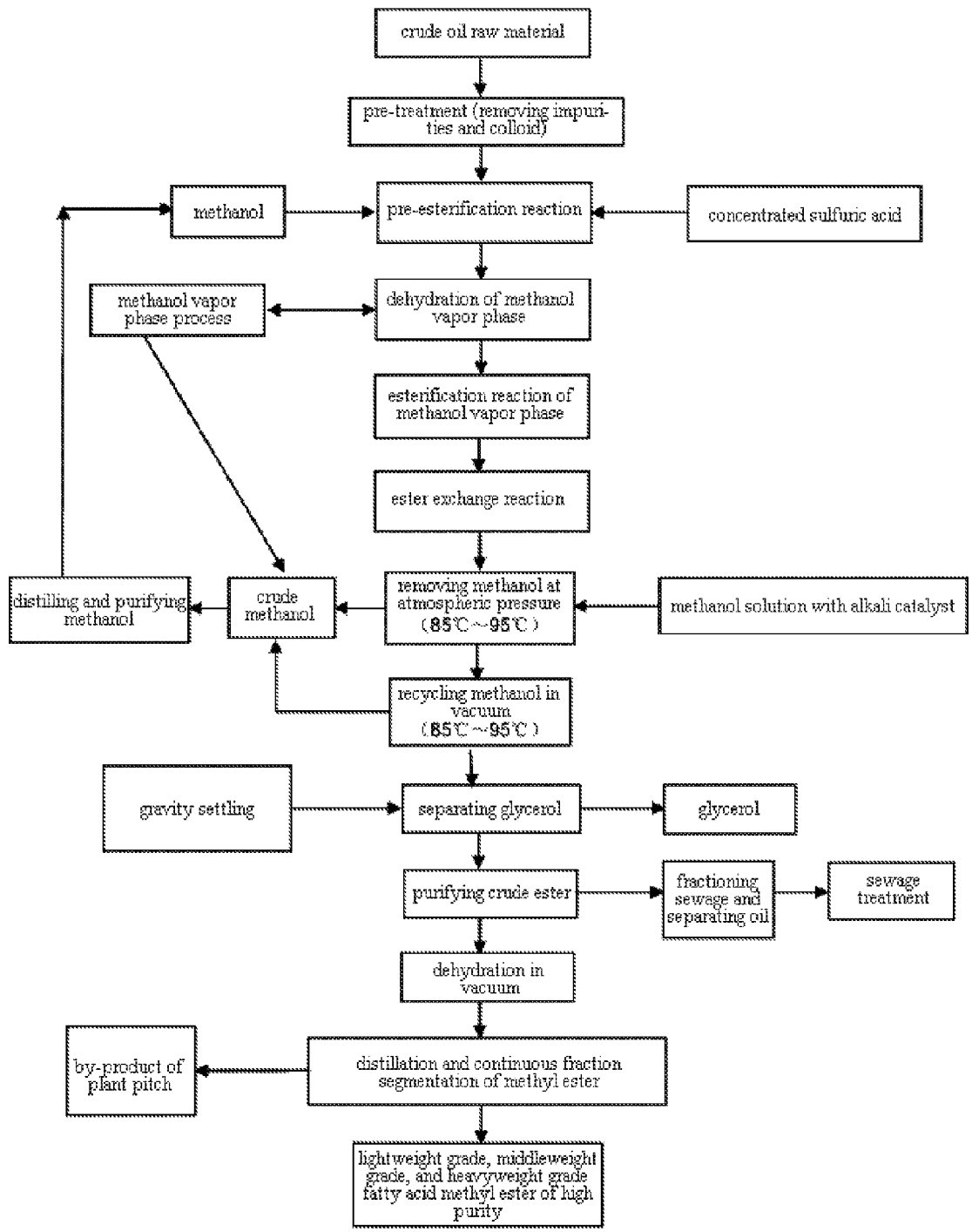
FIG. 2 is schematic diagram of technological process of an embodiment according to the method of the present invention.

In the method of the present invention, crude oil raw material is not limited, and can be trench oil, acid oil, neutral oils and fats, waste oils and fats with acid value of 50 KOHmg/g, or waste oils and fats with acid value of ≤150 KOHmg/g.

Crude oil raw material may be treated by water washing and vacuum dehydration. Water washing can adopt the following operations: at water (preferably 3% salt water) temperature of about 80° C., adding 5-7 vol % water of oil with stirring at 35-40 r/min within 7-10 min. (the content of water in purchased crude oil is generally 3-5%, so the actual amount of water added depends on the content of water in the crude oil, not adding or adding a little), reducing the stirring rate to 25-30 r/min, stirring for 10-15 min, then reducing the stirring rate to 15 r/min, stirring for 5-10 min, stopping stirring, standing for settling for 2-3 h, and discharging water and impurities.

The dehydration in vacuum may be performed by the following operations: heating oil to 95° C., and vacuumizing to −0.095 MPa, continuously proceeding the above, and pumping the dehydrated oil into a dehydrated oil storage tank.

In the method of the present invention, the reaction kettle may be common reaction kettle in the art according to technological demand and is not limited particularly. For example, a stainless steel reaction kettle may be used during the pre-treatment stage; an enamel reaction kettle may be used during the esterification and ester exchange stages; and a carbon steel reaction kettle may be used during the glycerol separating and water washing stage, preferably, the enamel reaction kettle may be used in the core process.

In the method of the present invention, two esterification processes are adopted. The first esterification process is called as "pre-esterification step", which is performed at a relatively low temperature of 70-80° C., and esterification conversion rate can reach above 70% in this step, thus reducing energy consumption and making the next esterification process more complete. In the second esterification process, a relatively high reaction temperature of 110-130° C. is adopted, and methanol in vapor phase is introduced from the bottom of the reaction kettle, which contributes to making full contact of oils and fats and methanol, and thus greatly improving the conversion rate. In addition, the second esterification process may control reaction time by detecting the acid value of the liquid phase system in the reaction kettle, and stop supplementing the vapor phase methanol when the acid value of the liquid phase system is ≤2. Most oils and fats have been esterified during the pre-esterification process, so unnecessary energy consumption would increase if the reaction time is not controlled during the esterification process, and by monitoring the acid value, the reaction time and the energy consumption may be greatly saved and the reaction process may be better monitored.

As used herein, during the esterification process, the concentrated sulfuric acid is common 98% concentrated sulfuric acid, the dosage thereof is 0.1-2 wt % of the pre-treated raw material, preferably 0.2-1 wt %, more preferably 0.3-0.6 wt % and most preferably 0.4-0.5 wt % (for example, can be 0.1, 0.2, 0.3, 0.4, 0.5, 0.6, 0.7, 0.8, 0.9, 1.0 wt %, etc.), and in the subsequent steps, there is no need to additionally add concentrated sulfuric acid. The dosage is greatly decreased relative to the prior art, thus reducing production cost.

The weight ratio of methanol to oils and fats or reaction material is controlled at (1:1)-(1:20), preferably (1:15)-(1:4), more preferably (1:10)-(1:5), (1:11)-(1:6) and (1:12)-(1:7) during, the pre-esterification process.

In the method of the present invention, the ester exchange reaction and the esterification reaction are carried out in the same reaction kettle, which is beneficial to save the equipment cost and decrease the operation complexity. After the esterification reaction is finished, the material is cooled to 70-80° C. and the ester exchange reaction may be performed immediately.

In the ester exchange reaction of the present invention, the alkali catalyst is the mixture of sodium hydroxide and potassium hydroxide with equal ratio (weight ratio of 1:1), and the final amount of alkali catalyst is added such that the pH value of the material in the reaction kettle is maintained in pH 8-9. Since a part of sulfuric acid can be brought away by vapor phase methanol and water, and the total amount of sulfuric acid is not constant during the previous vapor phase esterification process, the addition amount of alkali depends on pH value. In practical production, the weight ratio of alkaline mixture (without methanol) to oil (without methanol) is (0.1-2):100, generally is 0.5-0.9 wt %. As previously described, the use of solo sodium hydroxide as catalyst has four defects, which are not paid enough attention to in prior art. Considering easy agglomeration of sodium salt, good flowability of potassium salt, high cost of potassium hydroxide, comprehensive cost and pipeline blocking situation, through experiments and specific production tests (adopting mixture with various ratios), the present invention adopts the mixture of sodium hydroxide and potassium hydroxide with equal ratio, and with such a ratio, not only the pipeline blocking but also the problems of high cost and long dissolving time of potassium hydroxide are overcome.

The liquid after the ester exchange reaction is separated into two layers, the upper layer contains resultant crude fatty acid methyl ester and residual methanol, and the lower layer contains glycerol. The crude methanol is recycled into a crude methanol tank under atmospheric pressure, and the reaction material is pumped into a vacuum tank for removing methanol and methanol is further recycled into the crude methanol tank. Both the two steps can be performed at the temperature of 85-95° C. Since a large amount of alkali has reacted with sulfuric acid to produce salt during the reaction process, a small amount of acid or alkali is washed with water to enter sewage treatment system in purification of crude ester after separating glycerol.

In the method of the present invention, lower-layer glycerol is separated from methanol removed material through gravity settling action (for example, dynamic physical settling method, 8-40 n/min). The step requires no settling separator, because the separation by removing methanol in vacuum is more thorough than that by settling separator.

In the method of the present invention, after separation from glycerol, the crude fatty acid methyl ester may be further purified by water washing, dehydrated in vacuum, and distilled at the temperature of 220-260° C. under the pressure of (−0.090)-(−0.099) Mpa to obtain refined fatty acid methyl ester and by-product of plant pitch.

In a preferred embodiment of the method of the present invention, by adopting pre-esterificaiton reaction and vapor phase esterification reaction and through ester exchange, the conversion of fatty acid methyl ester is very sufficient, the impurities are relatively little, and the separation of various products is relatively simple, so fractions may be segmented by using a methyl ester distillation and segmentation system and adopting lateral line continuous distillation, such that the crude fatty acid methyl ester may be directly segmented into fraction products of four temperature intervals: a. ≤280° C.; 280-365° C.; c. 365-380° C.; and d. ≥380° C. (respectively corresponding to lightweight grade, middleweight grade, and heavyweight grade fatty acid methyl ester of high purity, and plant pitch) and the fatty acid methyl ester reaches colorless and tasteless high-quality grade. The distillation and segmentation system of methyl ester as mentioned above may be a commonly-used rectification system in petroleum refining industry, such as vacuum continuous rectification system.

The presently-disclosed subject matter is further illustrated by the following specific but non-limiting examples.

Example 1

1,200 kg of methanol is added into a batching pot in advance, then stirred, and 45 kg of concentrated sulfuric acid is added, and stirred well for use. 8 tons of trench oil recycled in a crude oil transfer tank is washed with water in a stainless steel water washing tank, dehydrated in vacuum, and then placed into an enamel reaction kettle together with the prepared sulfuric acid-methanol solution. The jacket of the reaction kettle is opened, and the reaction kettle is steam-heated to about 70° C. and maintained for 30 min. A steam inlet valve is continued to open wide, methanol is adjusted to return back to each valve, and the crude methanol condensed by a methanol condenser is recycled to a crude methanol tank. When the temperature of liquid phase reaches 110-115° C., a methanol inlet bottom valve of the reaction kettle is opened, a fresh methanol pump is turned on, a methanol flowmeter control valve is opened, the supplementation of the vapor phase methanol is started through a methanol vapor phase generator, and the feeding flow rate is controlled at 500 L/h; after 2 h, the sample is collected for detection; and when the acid value is ≤2, the addition of methanol is stopped. The reaction material in the reaction kettle is cooled to 70-80° C., and oil residue is discharged aperiodically until being basically discharged.

The potassium hydroxide-sodium hydroxide methanol solution is prepared while performing esterification reaction. Firstly 1,200 kg of methanol is pumped into an alkali catalyst methanol preparation tank, and 19 kg KOH and 19 kg NaOH are added slowly under stirring. After addition, stirring is continued until KOH and NaOH are completely dissolved in methanol.

When the temperature of reaction kettle is ≤70° C., the feeding valve of potassium hydroxide-sodium hydroxide methanol solution is opened, the prepared potassium hydroxide-sodium hydroxide methanol solution is added, and pH value is checked and guaranteed to be 8-9. If the pH value is smaller than 8, the potassium hydroxide-sodium hydroxide methanol solution is supplemented until pH is at 8-9. Simultaneously, a steam valve is opened, and heating is started.

The temperature of the ester exchange reaction is controlled at 70-80° C., methanol is subjected to total reflux reaction, and the time of stirring and refluxing is about 2-3 h. Then the refluxing is stopped, the valve of the crude methanol tank is opened, and the crude methanol is started to recycle into the crude methanol tank under atmospheric pressure. The recycling under atmospheric pressure is stopped and then the steam valve is closed when the temperature in the tank rises to 90-95° C. . The recycled crude methanol is pumped into the vacuum methanol removing tank, and recycled in vacuum at the temperature of 95° C. for 30 min until the vacuum degree rises to −0.95 MPa.

The material in the methanol removing tank is pumped into a glycerol separating and water washing tank with stirring using a drawing pump of the methanol removing tank, continued to stir for 10-40 min after pumping, and maintained a standstill for 1-2 h, and glycerol and impurities are separated.

After glycerol is separated out, 3-10 wt % water of the methyl ester (the temperature of the added water is 80-95° C.) or salt water with concentration of 1-5% is added, stirred for 10-50 min, stopped stirring, and statically precipitated for 2 h, and water is discharged.

The methyl ester is heated to 80-95° C., and continuously dehydrated under vacuum of (−0.090)-(−0.095) MPa in a vacuum dehydration tower, and the balance of oil feeding and oil discharging is maintained.

The obtained crude fatty acid methyl ester is subjected to rectification under the pressure of −0.099 Mpa in a methyl ester distillation system to obtain refined fatty acid methyl ester and plant pitch, and finished product of the biodiesel is segmented and transferred into a high-purity lightweight grade, middleweight grade and heavyweight grade fatty acid methyl ester storage tank according to different fractions and temperatures (a. ≤280° C.; b. 280-365° C.; c. 365-380° C.; and d. ≥380° C.).

Through detection, in the finished product of the biodiesel, the content of fatty acid methyl ester (total) is 98.5%, total glycerol content is 0.210, the density is 860.0, the acid value is 0.8, the viscosity is 4.1, the flash point is 130, the cetane value is 53, the sulfur content is 0.001, and the methanol content is 0.005 ppm (see specific results in table 1).

Through calculation, in the example, the total yield of fatty acid methyl ester is 96%, the esterification reaction conversion rate is 97%, and the ester exchange reaction conversion rate is 98%.

TABLE 1

Measured Physicochemical Indexes and Test Methods

| Item | Physico-chemical index | Test method |
|---|---|---|
| Chroma, number | 1.5 | GB/T 6540 |
| Density (20° C.) kg/m$^3$ | 860.0 | GB/T 1884 |
| Kinematic viscosity (40° C.)/mm$^2$ · S | 4.1 | GB/T 265 |
| Flash point/° C. | 132 | GB/T 261 |
| Cetane value | 53 | GB/T 386 |
| Condensation point/° C. | −5 | GB/T 510 |
| Iodine value g/100 g | 136 | GB/T 5532 |
| Sulfur content, % | 0.001 | GB/T 380 |
| 10% carbon residue distilled, % | 0.26 | GB/T 268 |
| Sulfate ash content, % | 0.01 | GB/T 2433 |
| Water content (mass percentage)/% | 0.05 | SH/T 260 |
| Mechanical impurity | 无 | GB/T 511 |
| Copper sheet corrosion (50° C., 3 h)/grade | 1a | GB/T 5096 |
| Acid value/(mgKOH/g) | 0.8 | GB/T 264 |
| Oxidation stability (110° C.)/h | 6.0 | SH/T 0175 |
| Methyl ester content (m/m) | 98.5 | EN 14103 |
| Free glycerol content (mass percentage)/% | 0.015 | ASTM D 6584 |
| Total glycerol content (mass percentage)/% | 0.210 | ASTM D 6584 |
| Distillation range: | | |
| 90% recycling temperature, ° C. | 345 | GB/T 6536 |
| 95% recycling temperature, ° C. | 360 | |

Example 2

The performance parameters of the biodiesel obtained in Example 1 and 0# GB fossil diesel are compared (according to GB 252-2000), and the results are shown in table 2.

TABLE 2

Comparison of the Measured Values of The Biodiesel of The Present Invention and the Parameters of Conventional Fossil Diesel

| Technical index | Biodiesel (measured value) | Conventional fossil diesel (standard requirement value) |
|---|---|---|
| Chroma, number | 1.5 | ≤3.5 |
| Sulfur content, %(m/m) | 0.001 | ≤0.03 |
| Acid value, mgKOH/100 mL | 0.8 | 7 (pH value) |
| 10% Carbon residue distilled, %(m/m) | 0.26 | ≤0.5 |
| Ash content, %(m/m) | 0.01 | ≤0.03 |
| Copper sheet corrosion (50° C., 3 h),/grade | 1a | ≤1 |
| Water content, %(V/V) | 0.05 | ≤0.05 |
| Mechanical impurity | 无 | 无 |
| Kinematic viscosity (20° C.), mm$^2$/S | 4.1 | 3.5-5.9 |
| Condensation point, ° C. | −5 | Spring and Autumn: ≤−5 Summer: ≤0 Winter: ≤−10 |
| Flash point (closed cup), ° C. | 132 | ≥55 |
| Cetane value | 53 | ≥45 |
| Distillation range: | | |
| 90% recycling temperature, ° C. | 345 | ≤360 |
| 95% recycling temperature, ° C. | 360 | ≤365 |

As seen from the results of table 2, the biodiesel prepared according to the method of the present invention is completely in conformity with or even higher than the basic technical requirements of 0# GB fossil diesel, and can substitute the fossil diesel for use.

Although the aforementioned general description and specific embodiments have described the present invention in detail, it is obvious to a person skilled in the art to modify or improve the present invention based thereon. Therefore, such modifications or improvements made without deviating from the spirit of the present invention belong to the protection scope of the present invention.

INDUSTRIAL PRACTICALITY

The present invention provides a method for preparing biodiesel from crude oils. The method comprises: pre-treating the crude oil raw material to remove impurities; pre-esterifying the pre-treated crude oil raw material under the effect of a catalyst; and then carrying out an ester exchange reaction in the presence of an alkali catalyst; recycling methanol, and separating glycerol, so as to obtain a crude fatty acid methyl ester; and subjecting the obtained fatty acid methyl ester to purification, distillation and segmentation to obtain a high-purity fatty acid methyl ester. The method provided by the present invention can subject various types of crude oils, especially waste oils and fats, to recycle to obtain biodiesel with excellent performance indexes; and compared to prior art, greatly saves energy consumption, lowers cost, and has great economic benefit and social benefit.

What is claimed is:

1. A method for preparing biodiesel from crude oils, comprising:
   1) providing crude oil raw material, and pre-treating the crude oil raw material to remove impurities;
   2) adding the pre-treated raw material into a reaction kettle;
   3) pre-esterification step: adding methanol and 0.1-2 wt % concentrated sulfuric acid by the weight of the pre-treated raw material into the reaction kettle, and maintaining at 70-100° C., for 30 min-2 h, wherein the weight ratio of methanol to the pre-treated raw material is (1:11)-(1:6) to provide pretreated material;
   4) esterification step of vapor phase: heating the pretreated material to 110-130° C., supplementing vapor phase methanol from the bottom of the reaction kettle under atmospheric pressure, reacting under the temperature until an acid value of liquid phase system is ≤2, and stopping supplementing methanol;
   5) ester exchange step: cooling the reaction material obtained in the step 4) to below 70° C., adding mixture of potassium hydroxide and sodium hydroxide with equal weight ratio in the same reaction kettle to maintain pH of the reaction material in the reaction kettle at 8-9, and then reacting at 70-90° C., for 2-3 h;
   6) recycling methanol, and separating glycerol via gravity settling, so as to obtain a crude fatty acid methyl ester; and
   7) subjecting the crude fatty acid methyl ester obtained in the step 6) to purification and distillation to obtain biodiesel.

2. The method according to claim 1, wherein the crude oil raw material is trench oil or acid oil.

3. The method according to claim 1 or 2, wherein the weight ratio of methanol to the pre-treated raw material in the step 3) is (1:15)-(1:4).

4. The method according to claim 1 or 2, wherein the distillation of crude fatty acid methyl ester in the step 7) is performed at the temperature of 220-260° C. under the pressure of (-0.090)-(-0.099) MPa, so as to obtain the biodiesel and plant pitch.

5. The method according to claim 1 or 2, wherein in the step 7), the crude fatty acid methyl ester is directly and continuously distilled and segmented into fraction products of four temperature intervals: a. ≤280° C.; b. 280-365° C.; c. 365-380° C.; and d. ≤380° C.

6. The method according to claim 1 or 2, wherein the recycling of methanol in the step 6) is performed via two steps: recycling at the temperature of 85-95° C. under atmospheric pressure and recycling at the temperature of 85-95° C. and vacuum.

7. The method according to claim 1 or 2, wherein the pre-treatment comprises water washing, dehydration in vacuum or the combination thereof.

8. The method according to claim 1, wherein the reaction kettle in step 3) is maintained at 70-80° C. for 30 min-2 h.

9. The method according to claim 1, wherein the reacting in step 5) is at 70-80° C., for 2-3 h.

* * * * *